US010058337B2

(12) United States Patent
Feibel et al.

(10) Patent No.: US 10,058,337 B2
(45) Date of Patent: Aug. 28, 2018

(54) TARGETING DEVICE FOR USE WITH SYSTEMS, METHODS, AND APPARATUSES FOR FUSION, STABILIZATION, AND/OR FIXATION OF BONES

(71) Applicants: Jonathan Feibel, Columbus, OH (US); Robert Gorsline, Columbus, OH (US)

(72) Inventors: Jonathan Feibel, Columbus, OH (US); Robert Gorsline, Columbus, OH (US); Nicholas Joseph Vallo, New Albany, OH (US); Christos Ragais, New Albany, OH (US); Christopher Brown, Columbus, OH (US); Christopher Hawker, Columbus, OH (US); Jeffrey J. Root, Columbus, OH (US)

( * ) Notice: Subject to any disclaimer, the term of this patent is extended or adjusted under 35 U.S.C. 154(b) by 0 days.

(21) Appl. No.: 15/886,959

(22) Filed: Feb. 2, 2018

(65) Prior Publication Data
US 2018/0168666 A1    Jun. 21, 2018

Related U.S. Application Data

(63) Continuation of application No. 14/562,613, filed on Dec. 5, 2014, now abandoned.

(60) Provisional application No. 61/912,512, filed on Dec. 5, 2013.

(51) Int. Cl.
 *A61B 17/17* (2006.01)

(52) U.S. Cl.
 CPC ...... *A61B 17/1725* (2013.01); *A61B 17/1775* (2016.11)

(58) Field of Classification Search
 CPC .. A61B 17/17; A61B 17/1725; A61B 17/1775
 See application file for complete search history.

(56) References Cited

PUBLICATIONS

Extended Search Report issued in European Application No. 14867901.2, dated Jun. 16, 2017.

*Primary Examiner* — Christopher Beccia
(74) *Attorney, Agent, or Firm* — Benesch, Friedlander, Coplan & Aronoff LLP (57) ABSTRACT

Various embodiments of a targeting device for use with systems, methods, and apparatuses for fusion, stabilization, and/or fixation of bones are disclosed. In one embodiment, a targeting device is provided, the targeting device comprising: a targeting arm including a targeting portion, a radial portion, and at least one aperture oriented in the targeting portion; a target lock; and a rotation arrestor including an arresting engagement portion, an elongated shaft, and a button operatively connected to the arresting engagement portion.

20 Claims, 5 Drawing Sheets

TARGETING DEVICE FOR USE WITH SYSTEMS, METHODS, AND APPARATUSES FOR FUSION, STABILIZATION, AND/OR FIXATION OF BONES

CROSS-REFERENCE TO RELATED APPLICATIONS

This application is a continuation of U.S. patent application Ser. No. 14/562,613, filed on Dec. 5, 2014, which claims priority from U.S. Provisional Patent Application No. 61/912,512, filed on Dec. 5, 2013, both of which are incorporated by reference herein in their entireties.

BACKGROUND

The implantation, use, and tensioning of orthopedic implanted devices for fusion, stabilization, and fixation of joints, fractures, and other fusions may involve various complicated processes and components.

When implanting an orthopedic device that is internally oriented in the human body, such as a nail, a rod, or the like, it may be difficult to properly and accurately target the desired site(s), e.g., at which to ream holes to accept transverse bolts, or the like, from outside the human body. The present application appreciates that targeting associated with use of systems, methods, and apparatuses for fusion, stabilization, and/or fixation of bones may be a challenging endeavor.

SUMMARY

In one embodiment, a targeting device is disclosed. The targeting device may include a targeting arm. The targeting arm may include a targeting portion. The targeting arm may include a radial portion. The targeting arm may include at least one lower aperture for targeting transverse holes in an orthopedic implanted device. The targeting arm may include at least one upper aperture for targeting transverse holes in the orthopedic implanted device. The targeting arm may include a hub including a central bore. The targeting arm may include a radial bore. The targeting device may also include a target lock. The target lock may include at least one indentation. The target lock may include a target lock bore. The target lock may include a locking lever. The targeting device may further include a rotation arrestor. The rotation arrestor may include an arresting engagement portion. The rotation arrestor may include an elongated shaft. The rotation arrestor may include a button operatively connected to the arresting engagement portion. The target lock may be operatively connected to the orthopedic implanted device. The locking lever may at least one of selectively rotationally restrain and selectively axially restrain the target lock relative to a support device. The at least one indentation may be engaged by the arresting engagement portion. The at least one indentation may selectively rotationally restrain the target lock relative to the hub and the central bore.

In another embodiment, a targeting device is provided, the targeting device comprising: a targeting arm including a targeting portion, a radial portion, and at least one aperture oriented in the targeting portion; a target lock; and a rotation arrestor including an arresting engagement portion, an elongated shaft, and a button operatively connected to the arresting engagement portion.

In another embodiment, a targeting device is provided, the targeting device comprising: a targeting arm including a targeting portion, a radial portion, at least one aperture oriented in the targeting portion, and a hub including a central bore, wherein the radial portion includes a radial bore; a target lock oriented within the central bore; and a rotation arrestor including an arresting engagement portion, an elongated shaft, and a button operatively connected to the arresting engagement portion, wherein the elongated shaft extends through the radial bore.

In one embodiment, a method for using a targeting device is disclosed, the method comprising: providing a targeting arm. The targeting arm may include at least one lower aperture for targeting a transverse hole in an orthopedic implanted device. The targeting arm may include at least one upper aperture for targeting a transverse hole in the orthopedic implanted device. The method may further comprise providing a target lock. The target lock may comprise at least one indentation. The method may further comprise providing a rotation arrestor. The rotation arrestor may include an arresting engagement portion. The rotation arrestor may include a button operatively connected to the arresting engagement portion. The method may further include aligning the targeting arm wherein the at least one lower aperture is aligned with a first transverse hole in the orthopedic implanted device. The method may further include extending a ream through the at least one lower aperture and reaming through a bone and the first transverse hole in the orthopedic implanted device. The method may further include removing the ream from the bone and the first transverse hole in the orthopedic implanted device. The method may further include depressing the button and disengaging the arresting engagement portion from the at least one indentation. The method may further include rotating the targeting arm relative to the target lock to a desired position. The method may further include releasing the button and engaging the arresting engagement portion with the at least one indentation. The method may further include aligning the targeting arm wherein the at least one upper aperture is aligned with a second transverse hole in the orthopedic implanted device. The method may further include extending a ream through the at least one upper aperture and reaming through a bone and the second transverse hole in the orthopedic implanted device.

In another embodiment, a method for using a targeting device is provided, the method comprising: providing a targeting arm including at least one aperture for targeting at least one transverse hole in an orthopedic implanted device; providing a target lock including at least one indentation; providing a rotation arrestor including an arresting engagement portion and a button operatively connected to the arresting engagement portion; aligning the targeting arm wherein the at least one aperture is aligned with a first transverse hole in the orthopedic implanted device; extending a ream through the at least one aperture and reaming through a bone and the first transverse hole in the orthopedic implanted device; removing the ream from the bone and the first transverse hole in the orthopedic implanted device; depressing the button and disengaging the arresting engagement portion from the at least one indentation; rotating the targeting arm relative to the target lock to a desired position; releasing the button and engaging the arresting engagement portion with the at least one indentation; aligning the targeting arm wherein the at least one aperture is aligned with a second transverse hole in the orthopedic implanted device; and extending a ream through the at least one aperture and reaming through a bone and the second transverse hole in the orthopedic implanted device.

BRIEF DESCRIPTION OF THE DRAWINGS

The accompanying figures, which are incorporated in and constitute a part of the specification, illustrate various example configurations and systems, and are used merely to illustrate various example embodiments. In the figures, like elements bear like reference numerals.

DETAILED DESCRIPTION

When installing an orthopedic implanted device, such as a nail through a patient's ankle (e.g., through the calcaneus and talus, and into the tibia), a surgeon may install the nail from the patient's heel. The nail may include at least one transverse, circular or oblong hole for accepting transverse bolts, for example, to attach the calcaneus, talus, and/or tibia to the nail. To effect the installation of these transverse bolts, a surgeon may ream holes through a patient's calcaneus, talus, and/or tibia, for example, at very specific points in order to allow the transverse bolt to pass through the circular or oblong holes in the nail. These holes may be reamed from outside the patient's body after the nail is installed, and as such, a surgeon may be unable to actually view the circular or oblong holes in the nail while reaming the transverse holes. It is understood that the holes to be reamed may require extremely precise placement, size, angle, and the like, so as to minimize movement between a transverse bolt and the reamed hole. It is understood that installing an orthopedic implanted device, including for example a nail, rod, or the like, in any portion of a patient's body, may require similar targeting.

The disclosed targeting devices may be used to allow a surgeon to accurately determine a desired location, e.g., to ream the transverse holes in order to properly align the reamed holes with the circular or oblong holes in the nail, rod, or the like.

Figure 1:
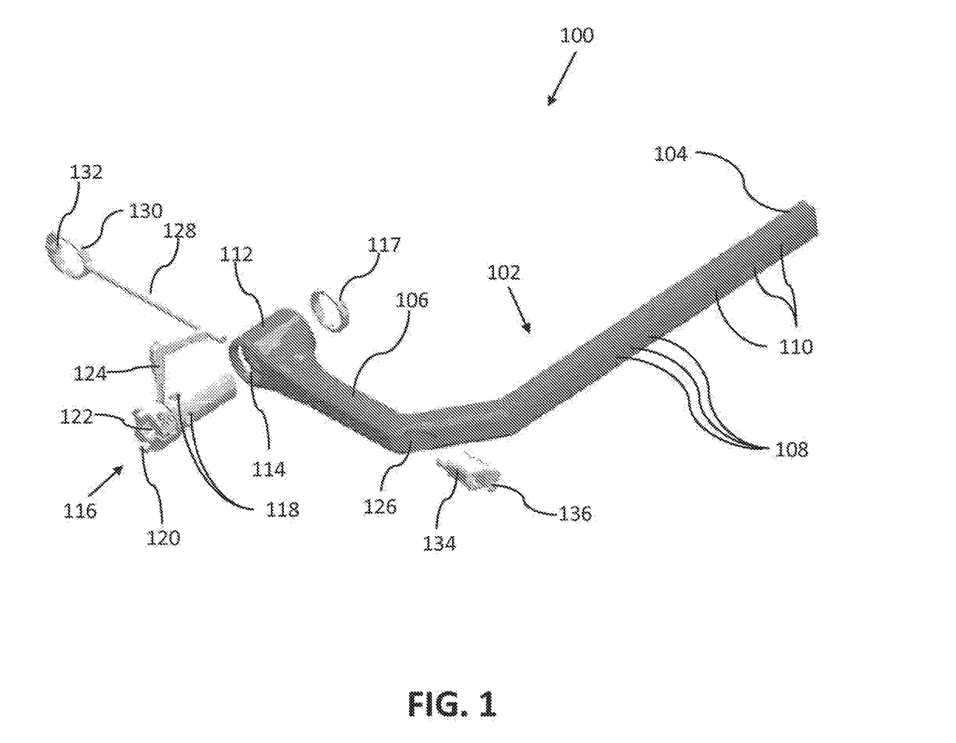
FIG. 1 is an exploded view of an example embodiment of a targeting device for use with systems, methods, and apparatuses for fusion, stabilization, and/or fixation of bones.

FIG. 1 is an exploded view of an example embodiment of a targeting device 100. Targeting device 100 may include a targeting arm 102 including a targeting portion 104 and a radial portion 106.

Targeting portion 104 and radial portion 106 may be oriented relative to one another in any of a variety of manners, including for example at an angle of about 90 degrees. Targeting portion 104 and radial portion 106 may be oriented relative to one another at an angle greater than about 90 degrees. Targeting portion 104 and radial portion 106 may be oriented relative to one another at an angle less than about 90 degrees. Orientation of targeting portion 104 relative to radial portion 106 may be dictated by any of a variety of factors, including for example the geometry of a patient's body, the device to be installed, the manner of reaming to be employed, and the like.

Targeting device 100 may include any of a variety of materials, including for example, a metal, an alloy, a polymer, a composite, and the like. Targeting device 100 may include materials capable of being sterilized, such as stainless steel (for example, surgical stainless steel). Targeting device 100 may include a titanium alloy. At least a portion of targeting device 100 may include a coating. Targeting device 100 may include a composite, such as a carbon fiber, fiberglass, and the like. Targeting arm 102 may include at least one of a radiolucent material and a radiopaque material. Targeting arm 102 may include a composite, such as a carbon fiber, fiberglass, and the like. Targeting portion 104 may include at least one of a radiolucent material and a radiopaque material. Targeting portion 104 may include a radiolucent material. Targeting portion 104 may include a composite, such as a carbon fiber, fiberglass, and the like.

Targeting portion 104 may include at least one transverse aperture. Targeting portion 104 may include at least one lower aperture 108. Targeting portion 104 may include at least one upper aperture 110. Targeting portion 104 may include at least one lower aperture 108 and at least one upper aperture 110.

At least one lower aperture 108 may be configured to target transverse holes in a nail (not shown). A nail (not shown) may include at least one transverse hole configured to accept a transverse bolt through at least one of the calcaneus and the talus. At least one lower aperture 108 may be configured to target at least one transverse hole in a nail (not shown) configured to accept a transverse bolt through at least one of the calcaneus and the talus. A nail (not shown) may include at least one transverse hole configured to accept a transverse bolt through at least one of the calcaneus the talus, and the tibia. At least one lower aperture 108 may be configured to target at least one transverse hole in a nail (not shown) configured to accept a transverse bolt through at least one of the calcaneus, the talus, and the tibia.

At least one lower aperture 108 may be configured to target transverse holes in a rod (not shown). A rod (not shown) may include at least one transverse hole configured to accept a transverse bolt through at least one of a patient's bones. At least one lower aperture 108 may be configured to target at least one transverse hole in a rod (not shown) configured to accept a transverse bolt through at least one of a patient's bones.

At least one upper aperture 110 may be configured to target transverse holes in a nail (not shown). A nail (not shown) may include at least one transverse hole configured to accept a transverse bolt through a patient's tibia. At least one upper aperture 110 may be configured to target at least one transverse hole in a nail (not shown) configured to accept a transverse bolt through the tibia. A nail (not shown) may include at least one transverse hole configured to accept a transverse bolt through at least one of the calcaneus the talus, and the tibia. At least one upper aperture 110 may be configured to target at least one transverse hole in a nail (not shown) configured to accept a transverse bolt through at least one of the calcaneus, the talus, and the tibia.

At least one upper aperture 110 may be configured to target transverse holes in a rod (not shown). A rod (not shown) may include at least one transverse hole configured to accept a transverse bolt through at least one of a patient's bones. At least one upper aperture 110 may be configured to target at least one transverse hole in a rod (not shown) configured to accept a transverse bolt through at least one of a patient's bones.

A nail (not shown) may include at least one transverse hole configured to accept a transverse bolt through at least one of the calcaneus, the talus, and the tibia. The at least one transverse hole may be oriented in a substantially medial-lateral direction, anterior-posterior direction, or both. For example, a nail (not shown) may include a series of transverse holes. The transverse holes may include at least one of: a hole configured to extend through a patient's calcaneus, a hole configured to extend through a patient's talus, and a hole configured to extend through a patient's tibia. In one example, the hole(s) in the nail configured to extend through a patient's calcaneus may extend in a substantially anterior-posterior direction. The hole(s) in the nail configured to extend through a patient's talus and/or tibia may extend in a substantially medial-lateral direction. In various embodiments, any of the at least one transverse hole(s) in a nail (not shown) may extend in a substantially medial-lateral direction, a substantially anterior-posterior direction, or at any angle from both a substantially medial-lateral direction and a substantially anterior-posterior direction.

The hole(s) in the nail may be configured to extend through any of a patient's bones. In another example, the nail may be replaced with any orthopedic implanted device, including for example a rod.

Targeting device 100 may include a hub 112. Hub 112 may include a central bore 114 substantially parallel to at least a portion of targeting portion 104. Central bore 114 may extend completely through hub 112. Central bore 114 may include a substantially constant diameter as it extends through hub 112. Central bore 114 may include a plurality of diameters as it extends through hub 112.

Targeting device 100 may include a target lock 116. Target lock 116 may be configured to be inserted into central bore 114. A locking ring 117 may be employed to engage target lock 116 in such a manner that target lock 116 may be axially restrained within hub 112 and central bore 114. A locking ring 117 may be employed to engage target lock 116 in such a manner that target lock 116 may be at least partially axially restrained within hub 112 and central bore 114.

Target lock 116 may include at least one indentation 118 configured to selectively rotationally restrain target lock relative to hub 112 and central bore 114. Target lock 116 may include at least one indentation 118 configured to at least partially selectively rotationally restrain target lock relative to hub 112 and central bore 114.

Target lock 116 may include at least one tab 120 configured to at least partially engage target lock 116 to a support device (not shown). At least one tab 120 may at least one of rotationally restrain, axially restrain, or both rotationally and axially restrain target lock 116 relative to a support device (not shown). A support device may include any device configured to support targeting device 100 while it is in use.

Target lock 116 may include a target lock bore 122 extending partially or completely through target lock 116 in a longitudinal direction. Target lock bore 122 may be configured to accept at least a portion of a support device (not shown).

Target lock 116 may include a locking lever 124 configured to at least one of selectively rotationally restrain and selectively axially restrain target lock 116 relative to a support device (not shown). Target lock 116 may include a locking lever 124 configured to at least one of partially selectively rotationally restrain and partially selectively axially restrain target lock 116 relative to a support device (not shown).

At least a portion of targeting arm 102 may include radial bore 126 configured to accept an elongated shaft 128 of a rotation arrestor 130. Radial bore 126 may extend through radial portion 106. Radial bore 126 may extend at least partially through radial portion 106. Elongated shaft 128 may extend through at least a portion of radial bore 126, and may be attached at one end to a button 134. Button 134 and elongated shaft 128 may be attached via any of a variety of fastening mechanisms, e.g., a screw 136. Elongated shaft 128 may be attached at another end to rotation arrestor 130. Rotation arrestor 130 may include an arresting engagement portion 132. Elongated shaft 128 may be attached to rotation arrestor 130 via any of a variety of fastening mechanism. Elongated shaft 128 may be integrally attached to rotation arrestor 130.

At least a portion of elongated shaft 128 and radial bore 126 may be operatively connected to a biasing member, such as a spring. The biasing member may be configured to bias elongated shaft 128, rotation arrestor 130, and arresting engagement portion 132 into radial bore 126. As illustrated in FIG. 1, the biasing member may bias elongated shaft 128, rotation arrestor 130, and arresting engagement portion 132 toward targeting portion 104. Arresting engagement portion 132 may selectively extend into central bore 114.

Target lock 116 may be inserted into central bore 114. At least one indentation 118 may be biased into engagement with arresting engagement portion 132. At least one indentation 118 may include a beveled edge configured to aid in engagement between indentation 118 and arresting engagement portion 132.

Indentation 118 may be substantially circular, and arresting engagement portion 132 may include a substantially circular profile. Indentation 118 may be any of a variety of shapes, including a groove, and engagement portion 132 may be any of a variety of shapes configured to substantially fit into indentation 118.

In practice, target lock 116 may be selectively attached to a nail (not shown), such that target lock 116 may be oriented in a desired rotational alignment with the nail. Targeting arm 102 may be rotated and selectively locked relative to the nail as a result of the selective engagement between arresting engagement portion 132 and at least one indentation 118. At least one indentation 118 may include four indentations oriented about 90 degrees relative to one another about the periphery of target lock 116. At least one indentation 118 may include two indentations oriented about 90 degrees relative to one another about the periphery of target lock 116. At least one indentation 118 may include any number of indentations oriented in any desired manner about the periphery of target lock 116.

Arresting engagement portion 132 and at least one indentation 118 may be selectively engaged and disengaged by a user depressing button 134. Button 134 may be attached to elongated shaft 128, which in turn may be attached to arresting engagement portion 132. Rotation arrestor 130 may be shaped like an oblong oval, or the like. Rotation arrestor 130 may permit linear travel while oriented about target lock 116. Rotation arrestor 130 may permit linear travel of rotation arrestor 130, substantially parallel to elongated shaft 128, while oriented about target lock 116. Central bore 114 may include a cutout portion configured to accept rotation arrestor 130 and permit movement of the same.

Figure 2:
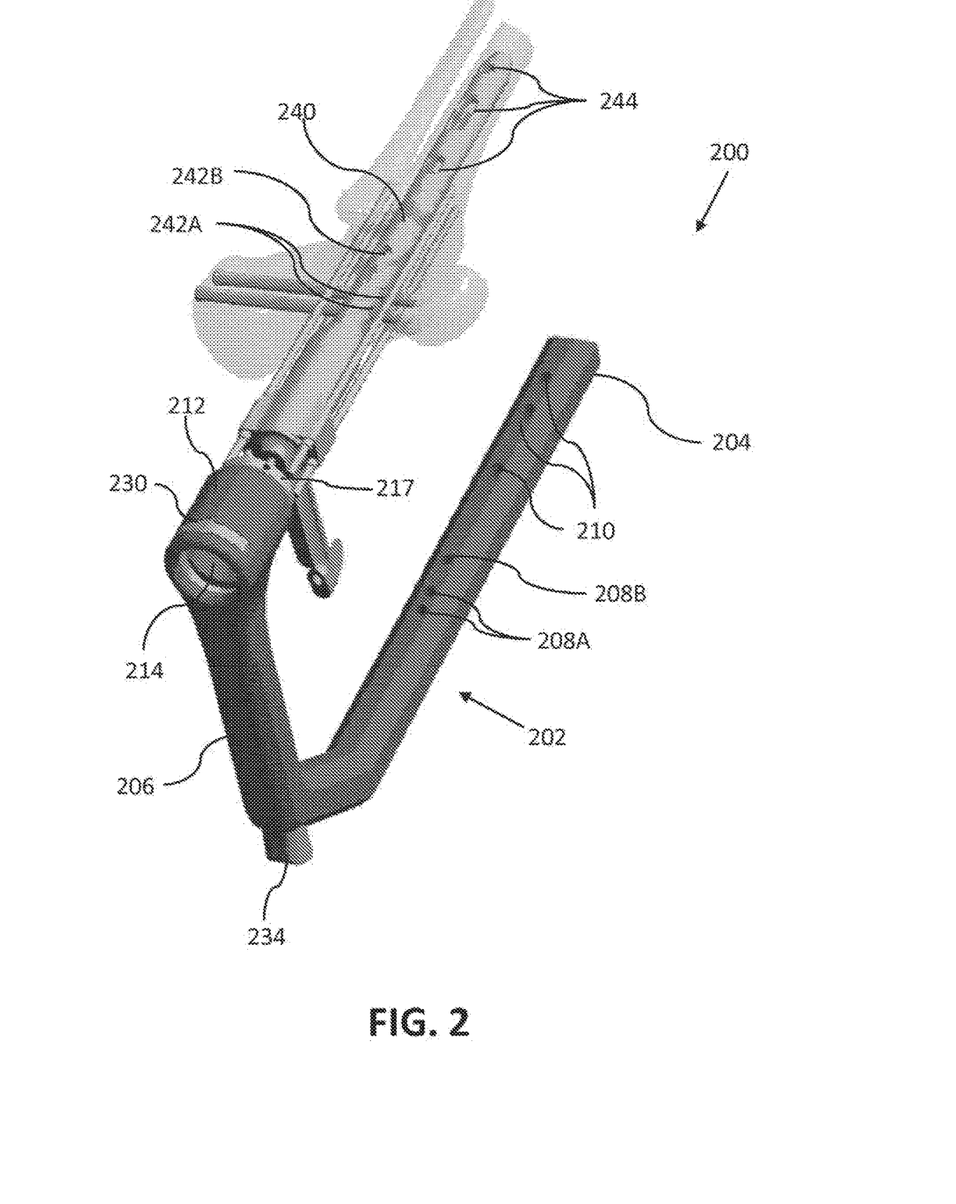
FIG. 2 is a perspective view of an example embodiment of a targeting device for use with systems, methods, and apparatuses for fusion, stabilization, and/or fixation of bones.

FIG. 2 is a perspective view of an example embodiment of a targeting device 200. Targeting device 200 may include a targeting arm 202, a targeting portion 204, and a radial portion 206.

Targeting portion 204 may include at least one lower aperture 208A and 208B and at least one upper aperture 210. Lower aperture 208A, 208B may be configured to target transverse holes 242A, 242B in a nail 240. Lower aperture 208A may be configured to target transverse holes 242A corresponding to a patient's calcaneus, such that holes drilled in this region may be used to attach the patient's calcaneus to the nail. Lower aperture 208B may be configured to target transverse holes 242B corresponding to a patient's talus, such that holes drilled in this region may be used to attach the patient's talus to the nail.

Upper aperture 210 may be configured to target transverse holes 244 in nail 240. Upper aperture 210 may be configured to target transverse holes 244 corresponding to a patient's tibia, such that holes drilled in this region may be used to attach the patient's tibia to the nail.

Targeting arm 202 may further include a hub 212, a central bore 214, a locking ring 217, and a rotation arrestor 230 operatively connected to a button 234.

In practice, targeting arm 202 may be oriented such that at least one lower aperture, such as lower aperture 208A, may be oriented substantially aligned with transverse holes 242A corresponding to a patient's calcaneus. Targeting arm 202 may be locked into place via engagement between an arresting engagement portion (not shown) and at least one indentation (not shown) in a target lock (not shown). A reamer may be inserted through at least one lower aperture 208A and extended to contact the patient's bone and ream through transverse hole 242A. Where multiple transverse holes 242A are present, the step described in this paragraph may be repeated for each such transverse hole 242A. Transverse holes 242A may be oriented in a substantially anterior-posterior direction. Transverse holes 242A may be oriented in a substantially medial-transverse direction.

Following reaming of transverse hole 242A, a user may depress button 234 causing disengagement of an arresting engagement portion from at least one indentation, at which point targeting arm 202 may be rotated by a desired amount, e.g., about 90 degrees. The arresting engagement portion may be reengaged to the at least one indentation found at the desired position by a user's release of button 234. At this point, for example, lower aperture 208B may be substantially aligned with transverse hole 242B. A reamer may be inserted through at least one lower aperture 208B, extended to contact the patient's bone, and ream through transverse hole 242B. Additionally, a user may ream transverse holes 244 in the same manner, but by extending a reamer through at least one upper aperture 210. Transverse hole 242B and 244 may be oriented in a substantially medial-transverse direction. Transverse hole 242B and 244 may be oriented in a substantially anterior-posterior direction.

It is contemplated that any of various holes may be reamed in any order. The example method of using targeting arm 202 recited herein is simply one of various possibilities. It is also contemplated that a user may orient targeting arm 202 on any one or more of a medial side, transverse side, anterior side, and posterior side, or at an angle between any of such sides, in order to perform the reaming function. Preference, position of arteries, veins, ligaments, and the like may influence the desired direction of entry for reaming. It is further contemplated that targeting device 200 may be used with any of a variety of bones, joints, and the like, and should not be interpreted as being limited to use with a calcaneus, talus, and tibia. It is further contemplated that targeting device 200 may be used with any of a variety of orthopedic implanted devices, and should not be interpreted as being limited to use with a nail.

Figure 3:
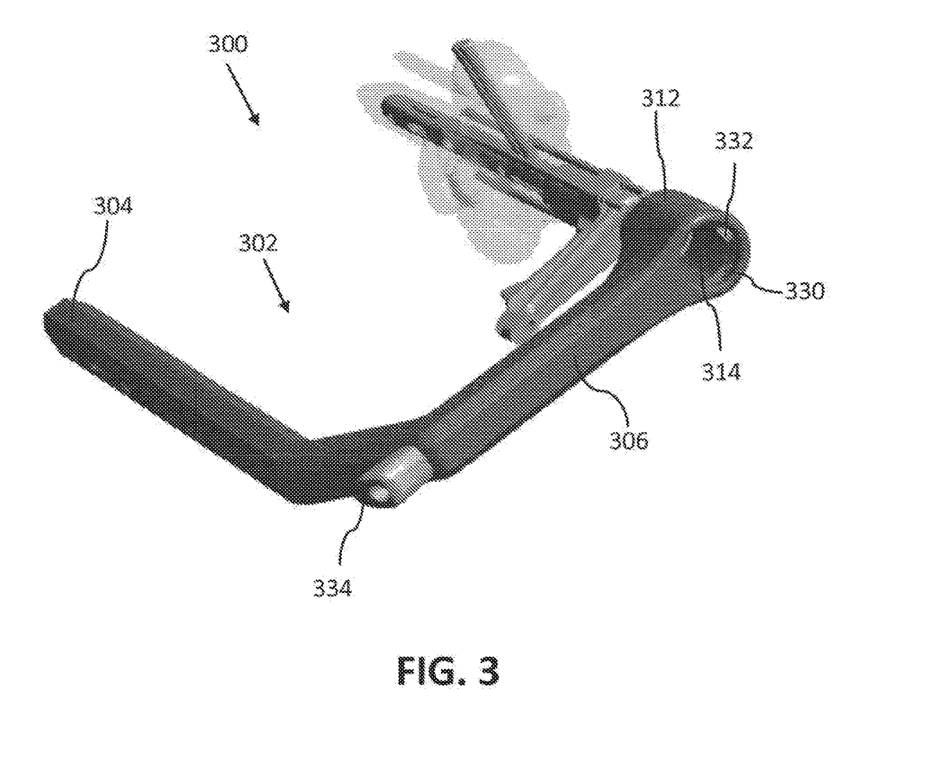
FIG. 3 is a perspective view of an example embodiment of a targeting device for use with systems, methods, and apparatuses for fusion, stabilization, and/or fixation of bones.

FIG. 3 is a perspective view of an example embodiment of a targeting device 300. Targeting device 300 may include a targeting arm 302, a targeting portion 304, and a radial portion 306. Targeting device 300 may include a hub 312, a central bore 314, a rotation arrestor 330, an arresting engagement portion 332, and a button 334 operatively connected to rotation arrestor 330 and arresting engagement portion 332.

Figure 4:
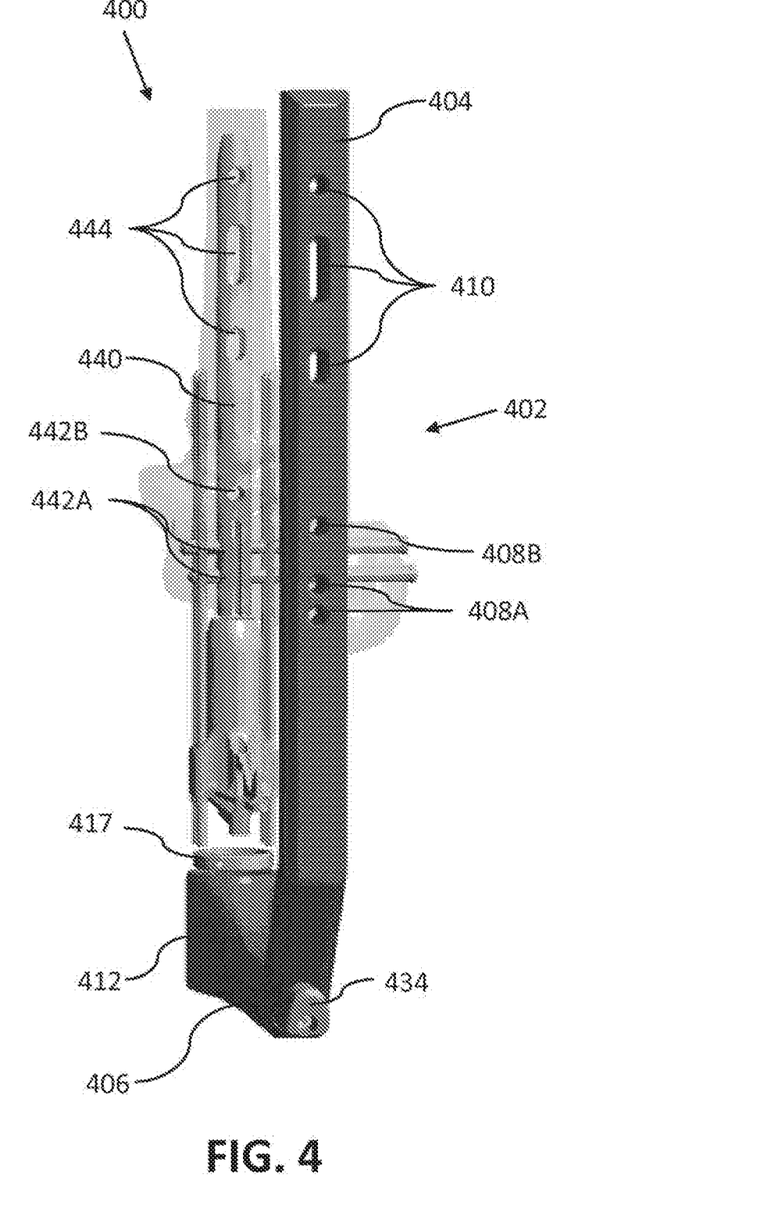
FIG. 4 is a perspective view of an example embodiment of a targeting device for use with systems, methods, and apparatuses for fusion, stabilization, and/or fixation of bones.

FIG. 4 is a perspective view of an example embodiment of a targeting device 400. Targeting device 400 may include a targeting arm 402, a targeting portion 404, and a radial portion 406. Targeting device 400 may include a hub 412, a locking ring 417, and a button 434.

Targeting portion 404 may include at least one lower aperture 408A, 408B and at least one upper aperture 410. The at least one lower apertures 408A, 408B may be configured to substantially align with transverse holes 442A, 442B of a nail 440. At least one upper aperture 410 may be configured to substantially align with transverse holes 444.

Figure 5:
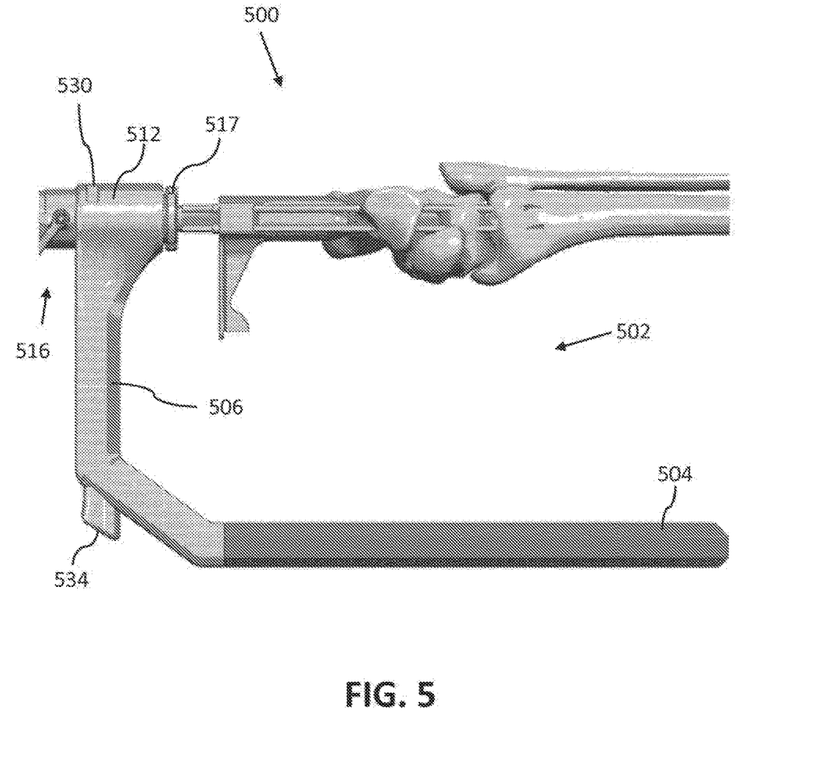
FIG. 5 is a side view of an example embodiment of a targeting device for use with systems, methods, and apparatuses for fusion, stabilization, and/or fixation of bones.

FIG. 5 is a side view of an example embodiment of a targeting device 500. Targeting device 500 may include a targeting arm 502, a targeting portion 504, and a radial portion 506. Targeting device 500 may include a hub 512, a target lock 516, a locking ring 517, a rotation arrestor 530, and a button 534 operatively connected to rotation arrestor 530.

At least a portion of targeting portion 504 may include a radiolucent material. In another embodiment, at least a portion of radial portion 506 may include a stainless steel. At least a portion of targeting device 500 may include a coating.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available or prudent in manufacturing. To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. A targeting device comprising:
a targeting arm including a targeting portion having one or more apertures for targeting reamer apertures, a hub having a bore, and a radial portion reaching radially between the hub and the targeting portion;
a target lock configured to rotate within the bore relative to the targeting arm between rotational orientations that are spaced apart about the hub at angles corresponding to predetermined locations of reamer apertures; and
a rotation arrestor having an arresting engagement portion configured to move into blocking engagement with the target lock to block rotation of the target lock within the bore relative to the targeting arm, and further configured to move into blocking engagement with the targeting arm only when the targeting arm and the target lock are located in one of the spaced apart rotational orientations.

2. The targeting device of claim 1, wherein the target lock is configured to rotate within the bore relative to the targeting arm in opposite directions about the hub, and the arresting engagement portion of the rotation arrestor is configured to block rotation of the target lock within the bore relative to the targeting arm in both of the opposite directions simultaneously.

3. The targeting device of claim 1, wherein the angles include an angle of about 90 degrees or more about the hub.

4. The targeting device of claim 1, wherein the rotation arrestor is configured to encircle the target lock within the bore, the rotation arrestor has an inner periphery at which the arresting engagement portion projects radially inward, and the target lock has an outer periphery with indentations configured to receive the arresting engagement portion at selected locations about the outer periphery.

5. The targeting device of claim 4, wherein the inner periphery of the rotation arrestor is configured to enable radial movement of the arresting engagement portion into engagement with an indentation on the target lock upon movement of the rotation arrestor laterally within the bore.

6. The targeting device of claim 4, wherein the indentations include two indentations that are spaced apart about the outer periphery of the target lock at an angle of about 90 degrees or more, and the target lock is free of indentations configured to receive the arresting engagement portion of the rotation arrestor at peripheral locations between the two indentations.

7. The targeting device of claim 4, wherein the indentations are openings at the outer periphery of the target lock, and the arresting engagement portion is configured for movement radially into and out of a selected opening.

8. The targeting device of claim 7, wherein the arresting engagement portion of the rotation arrestor is configured as a radially projecting pin.

9. A targeting device comprising:
a targeting arm including a targeting portion having one or more apertures for targeting reamer apertures, a hub having a bore, and a radial portion reaching radially between the hub and the targeting portion;
a target lock configured to rotate within the bore relative to the targeting arm between rotational orientations that are spaced apart about the hub at angles corresponding to predetermined locations of reamer apertures; and
a rotation arrestor having an arresting engagement portion configured to move into blocking engagement with the target lock to block rotation of the target lock within the bore relative to the targeting arm;
wherein the rotation arrestor is configured to encircle the target lock within the bore, the rotation arrestor has an inner periphery at which the arresting engagement portion projects radially inward, and the target lock has an outer periphery with openings configured to receive the arresting engagement portion at selected locations about the outer periphery.

10. The targeting device of claim 9, wherein the arresting engagement portion of the rotation arrestor is configured as a radially projecting pin.

11. The targeting device of claim 9, wherein the inner periphery of the rotation arrestor is configured to enable radial movement of the arresting engagement portion into and out of a selected opening on the target lock upon movement of the rotation arrestor laterally within the bore.

12. The targeting device of claim 9, wherein the openings include two openings that are spaced apart about the outer periphery of the target lock at an angle of about 90 degrees or more, and the target lock is free of openings configured to receive the arresting engagement portion of the rotation arrestor at peripheral locations between the two openings.

13. The targeting device of claim 9, wherein the target lock is configured to rotate within the bore relative to the targeting arm in opposite directions about the hub, and the arresting engagement portion of the rotation arrestor is configured to block rotation of the target lock within the bore relative to the targeting arm in both of the opposite directions simultaneously.

14. The targeting device of claim 9, wherein the angles include an angle of about 90 degrees or more about the hub.

15. A targeting device comprising:
a targeting arm including a targeting portion having one or more apertures for targeting reamer apertures, a hub having a bore, and a radial portion reaching radially between the hub and the targeting portion;
a target lock configured to rotate in opposite directions within the bore relative to the targeting arm between rotational orientations that are spaced apart about the hub at angles corresponding to predetermined locations of reamer apertures; and
a rotation arrestor having an arresting engagement portion configured to move into blocking engagement with the target lock to block rotation of the target lock within the bore relative to the targeting arm, and further configured to block rotation of the target lock within the bore relative to the targeting arm in both of the opposite directions simultaneously;
wherein the rotation arrestor is configured to encircle the target lock within the bore, the rotation arrestor has an inner periphery at which the arresting engagement portion projects radially inward, and the target lock has an outer periphery with openings configured to receive the arresting engagement portion at selected locations about the outer periphery; and
wherein the arresting engagement portion of the rotation arrestor is configured as a radially projecting pin.

16. The targeting device of claim 15, wherein the inner periphery of the rotation arrestor is configured to enable radial movement of the arresting engagement portion into and out of a selected opening on the target lock upon movement of the rotation arrestor laterally within the bore.

17. The targeting device of claim 15, wherein the openings include two openings that are spaced apart about the outer periphery of the target lock at an angle of about 90 degrees or more, and the target lock is free of openings configured to receive the arresting engagement portion of the rotation arrestor at peripheral locations between the two openings.

18. The targeting device of claim 15, wherein the target lock is further configured to move into blocking engagement with the targeting arm only when the targeting arm and the target lock are located in one of the spaced apart rotational orientations.

19. The targeting device of claim 15, wherein the angles include an angle of about 90 degrees or more about the hub.

20. The targeting device of claim 15, wherein the openings include two openings that are spaced apart about the outer periphery of the target lock at an angle of about 90 degrees or more, and the target lock is free of openings configured to receive the arresting engagement portion of the rotation arrestor at peripheral locations between the two openings.

* * * * *